United States Patent
Brown et al.

(10) Patent No.: US 9,051,558 B2
(45) Date of Patent: Jun. 9, 2015

(54) METHOD FOR IMMUNE CELL-ASSISTED BACTERIAL CULTURING

(71) Applicant: MRIGlobal, Kansas City, MO (US)

(72) Inventors: Kelly Brown, Melbourne, FL (US); Richard Winegar, Palm Bay, FL (US); Jacqueline Bortzner, Melbourne, FL (US); Nicole Moritz, Indialantic, FL (US); Stephanie Sorrell, Palm Bay, FL (US)

(73) Assignee: MRIGLOBAL, Kansas City, MI (US)

( * ) Notice: Subject to any disclaimer, the term of this patent is extended or adjusted under 35 U.S.C. 154(b) by 0 days.

(21) Appl. No.: 13/972,888

(22) Filed: Aug. 21, 2013

(65) Prior Publication Data

US 2014/0057272 A1 Feb. 27, 2014

Related U.S. Application Data

(60) Provisional application No. 61/691,398, filed on Aug. 21, 2012.

(51) Int. Cl.
*C12N 1/00* (2006.01)
*C12N 1/12* (2006.01)
*C12N 1/20* (2006.01)
*C12Q 1/04* (2006.01)

(52) U.S. Cl.
CPC ... *C12N 1/20* (2013.01); *C12Q 1/04* (2013.01)

(58) Field of Classification Search
CPC .................................................. C12N 1/20
See application file for complete search history.

(56) References Cited

PUBLICATIONS

Revez et al (Life-Threatening Dermatoses and Emergencies in Dermatology, 2009, p. 254).*

Kong, Heidi H., Skin microbiome: geonomics-based insights into the diversity and role of skin microbes, Trends Mol Med., Jun. 2011, pp. 320-328, Volume-issued No. 17(6).

Abdelhakim Ben Nasr, Judith Haithcoat, Joseph E. Masterson, John S. Gunn, Tonyia Eaves-Pyles, and Gary R. Klimpel, Critical role for serum opsonins and complement receptors CR3 (CD11b/CD18) and CR4 (CD11c/CD18) in phagocytosis of *Francisella tularensis* by human dendritic cells (DC): upatke of *Francisella* leads to activation of immature DC and intracellular survival of bacteria, Journal of Leukocyte Biology, Oct. 2006, pp. 774-786, vol. 80.

B. Rafferty, D. Jönsson, S. Kalachikov, R. T. Demmer, R. Nowygrod, M.S.V. Elkind, H. Bush Jr. and E. Kozarkov, Impact of monocytic cells on recovery of uncultivable bacteria from atherosclerotic lesions, Journal of Internal Medicine, 2011, pp. 273-280, The Association for the Publication of the Journal of Internal Medicine.

Terry C. Dixon, Amin A. Fadl, Theresa M. Koehler, Joel A. Swanson and Philip C. Hanna, Early *Bacillus anthracis*-macrophage interactions: intracellular survival and escape, Cellular Microbiology, 2000, pp. 453-463, Volume-issue No. 2(6), Blackwell Science Ltd.

Matthew A. Weiner and Philip C. Hanna, Macrophage-Medicated Germination of *Bacillus anthracis* Endospores Requires the gerH Operon, Infection and Immunity, Date: Jul. 2003, pp. 3954-3959, Volume-issue No. 71(7), American Society for Microbiology.

John A. Ireland and Philip C. Hanna, Macrophage-Enhanced Germination of *Bacillus anthracis* Endospores Requires gerS, Infection and Immunity, Oct. 2002, pp. 5870-5872, Volume-issue No. 70(10), American Society for Microbiology.

* cited by examiner

*Primary Examiner* — Albert Navarro

(74) *Attorney, Agent, or Firm* — Husch Blackwell LLP; Samuel Digirolamo

(57) ABSTRACT

A method of culturing fastidious bacteria where a conditioned cell culture medium is prepared in which eukaryotic cells have been cultured, but where the medium is substantially free of the cultured cells. Fastidious bacteria are cultured in the medium. The conditioned cell culture medium can contain secreted factors from the cells. These factors promote the growth of the fastidious bacteria. The fastidious bacterial culture is maintained for a time period sufficient for the fastidious bacteria to multiply. The fastidious bacteria are analyzed using PCR, DNA sequencing or microbiology characterization.

18 Claims, No Drawings

METHOD FOR IMMUNE CELL-ASSISTED BACTERIAL CULTURING

CROSS-REFERENCE TO RELATED APPLICATIONS

This application claims the benefit of U.S. Provisional Patent Application No. 61/691,398 having a filing date of Aug. 21, 2012. The disclosure and teaching of the application identified above is hereby incorporated by reference.

STATEMENT REGARDING FEDERALLY SPONSORED RESEARCH OR DEVELOPMENT

The present invention was made with United States governmental support pursuant to contract HSHQDC-10-C-00141 with the Department of Homeland Security.

BACKGROUND OF THE INVENTION

The malevolent use of biological agents as weapons by terrorist groups or rogue states continues to be a threat to the security of every country in the world. Successfully recovering bacterial bioweapons from a crime scene is an important aspect of a criminal investigation to help determine the source of the threat. In addition, the diagnosis of patients with bacterial infections in a hospital or clinical application is important.

Exploitation of pathogenic bacteria as bioweapons typically requires the release of the bacteria into the environment. Environmental releases can be accomplished using a variety of approaches. Crop duster aircraft, tank sprayers, hand sprayers, and pressurized containers can be used to disseminate aerosolized bacteria, viruses, fungi and other pathogens into the environment. Additionally, liquids or powders containing pathogens can be dispensed onto foods at restaurants, injected into foods, or used to contaminate objects handled regularly by a large number of people.

There are virtually limitless scenarios that can be envisioned for introducing pathogens into the environment. A wide array of potential surfaces can be exposed to these bioweapons. The variety of methods for disseminating bioweapons and the many surfaces and matrices that the weapons may encounter present significant challenges for effective environmental sampling for bioweapons. Nevertheless, pathogens such as bacteria remaining in the environment subsequent to a biological attack provide a potentially rich source of evidence for use in criminal investigations.

Environmental or clinical samples containing bacteria can be analyzed for target molecular signatures using polymerase chain reaction (PCR)-based methodology. PCR-based approaches often provide the first indication of the presence of bacterial threat organisms in an environmental sample. These approaches are typically highly sensitive and robust. Nevertheless, information obtained using PCR-based approaches is incomplete. The indication that any given bacterial threat agent is present in an environmental matrix is typically a consequence of obtaining positive results from several target genes from that organism.

However, using PCR-based methods alone, it is often impossible to determine if all of the targets present in the sample originate from one single bacterium, or several natural-occurring, avirulent variant organisms, each carrying a portion of the nucleic acid encoding the virulence determinants. Mechanisms of DNA exchange (including conjugation, natural transformation and DNA scavenging) and plasmid loss can occur between bacteria in nature and complicate the interpretation of molecular analyses of environmental samples. The only way to ensure that an environmental sample testing positive for a bacterial threat agent using PCR-based approaches is actually positive is to isolate and culture bacteria from the sample. Bacteria grown from environmental isolates can be rapidly identified using PCR analysis. Therefore, live culture analysis is critical for verifying the presence of target bacteria in a sample that tests positive by PCR analysis.

The successful isolation, culturing, and analysis of bacteria from environmental or patient samples provide an opportunity to gather additional types of information vital for source attribution or diagnosis purposes. Potential information obtained from successful isolation of these bacteria includes: (1) DNA sequence and genotyping data that can provide clues to the origin of the bacteria, (2) phenotypic analysis and characterization including determination of antibiotic susceptibility profiles (culture "fingerprints"), (3) serotypic characterization, (4) bacteriophage susceptibility characterization, and (5) viability/virulence of the organisms.

Therefore, bacterial weapons remaining in the environment subsequent to a biological attack provide a potentially rich source of information to support a criminal investigation. In order to be useful in this manner, however, the bacteria must be successfully isolated from the environment and cultured. Successful isolation and culturing of bacterial agents from the environment is a critical aspect of the bio forensics challenge. Therefore, it would be beneficial to have a method for culturing and growing bacteria in a manner that permitted analysis of the bacteria.

A daunting challenge of microbiology is effective culturing of fastidious bacteria from environmental sample matrices or diagnostic samples. Fastidious bacteria require specialized environments and are extremely difficult, if not impossible, to grow in a typical laboratory setting. One reason for this is the highly complex nutritional requirements of fastidious bacteria are usually impossible to replicate in the laboratory using classical culturing methods. The bacteriological threat agents of interest to governmental agencies such as the US Department of Homeland Security (DHS) have all undergone exquisite adaptation to grow as successful pathogens within the context of mammalian host systems. Isolation of these fastidious bacteria from environmental samples is difficult and the number of matrices can be quite diverse preventing a single isolation method to be employed.

In reviewing the literature relating to pathogenesis, it was found that spores of *Bacillus anthracis*, the causative agent of anthrax, are induced to germinate and grow robustly when placed in the environment of macrophages in vitro. *B. anthracis* spores placed in the culture medium used for growing macrophages (but lacking the macrophages) do not germinate. [Dixon, et. al., (2000) *Cell Microbol*, 2:453-463; Ireland and Hanna, (2002) *Infect Immun*, 70:5870-5872].

Hanna and co-workers noted that macrophages are the human body's first line of defense against infection by *B. anthracis*, but that during the initial stages of anthrax, the bacteria are engulfed by, and multiply within, macrophages. Those workers also reported that *B. anthracis* spores are induced to germinate and multiply in vitro when in the proximity of the macrophages. No engulfment, or even contact, is required for this effect, suggesting that the macrophages secrete a "factor" or "factors" to simulate multiplication of the *B. anthracis* in these studies. [Weiner and Hanna, (2003) *Infect Immun*, 71:3954-3959]. Therefore, it is evident that *B. anthracis* has adapted well to the host immune response; the bacteria appear to exploit the features of the immune response to enhance their own growth and disease progression.

These reports of Hanna and co-workers were observations made regarding macrophage interactions with the non-fastidious bacterium, *B. anthracis*, and not a process by which to isolate and grow fastidious bacteria. Fastidious bacteria including, but not limited to: *Haemophilus influenza, Helicobacter pylori, Bordetella pertussis* and other *Bordetella* species, *B. fragilis, Mycobacterium tuberculosis, Legionella* species, *Spirochetes, Klebsiella* spp., *Brucella* species, *Francisella tularensis, Leptospira* species, *Borrelia burgdorferi, Bartonella* species, *Listeria* species, *Bordetella* species, *Eikenella corrodens, Pasteurella* species, *Haemophilus* species, *Chlamydia* species, *Camphylobacter* species, *Acinetobacter* species, *Mycoplasma* species, *Fusobacterium* species, *Corynebacteria* species, *Moraxella* species, *Pseudomonas* species, and *Neisseria* species require more nuanced growth conditions.

It would be beneficial to have a method for culturing fastidious bacteria that would be applicable to fastidious pathogenic bacteria. In particular, it would be beneficial to have a method for culturing fastidious bacterial pathogens that encounter the alveolar macrophages during the initial stages of disease development. The disclosure that follows discloses one such method.

SUMMARY OF THE INVENTION

Successful recovery of bacterial bioweapons from crime scenes is an important aspect of a criminal investigation. Bacterial bioweapons, expanded in culture, provide a potentially valuable source of information relevant to source attribution. Bacterial bioweapon cells are sometimes fastidious pathogens; furthermore, these cells are sometimes stressed due to aerosolization procedures or environmental exposure. These bacteria are highly recalcitrant to culturing from environmental matrices using classical culturing approaches. Immune cell-assisted culturing as described hereinafter is a novel culturing approach that exploits naturally occurring interactions between fastidious bacteria and macrophage (or monocyte) secretions to stimulate bacterial growth. This method of immune cell-assisted bacterial culturing is useful for culturing fastidious pathogens from both environmental samples and diagnostic samples.

Monocytes are phagocytic white cells that are present in the blood stream and further differentiate into macrophages that are also phagocytic white cells present in the tissues. The two cell types are very similar and differ mostly in the proteins they express. Either cell type or a mixture of both types can be used in a contemplated method. For convenience and ease of expression, both cell types are referred to as macrophages or "immune cells." During immune cell-assisted culturing, fastidious bacteria are co-cultured under prescribed conditions on standard laboratory media with macrophages prior to recovery.

In particular, a method of the present invention is illustratively used to culture *F. tularensis*, a fastidious bacterium, that exploits host cell-bacterial interactions that occur during the very early stages of bacterial pathogenesis. This method, termed "immune cell-assisted bacterial culturing" (IC-ABC) provides an approach to stimulate the growth of bioweapon bacteria isolated from environmental matrices or bacterial pathogens from diagnostic samples that are recalcitrant to culturing using traditional methodologies. Included herein are data that illustrate the application of immune cell-assisted culturing to one vaccine strain of *F. tularensis* (Live Vaccine Strain (LVS)) and one virulent strain of *F. tularensis* (WY96-3418).

DETAILED DESCRIPTION OF THE INVENTION

There is provided herein a method of culturing fastidious bacteria where a conditioned cell culture medium is prepared in which mammalian macrophages have been cultured, but where the medium is substantially free of the cultured macrophages. Fastidious bacteria are cultured in the medium. The conditioned cell culture medium can contain secreted factors from the macrophage. These factors promote the growth of the fastidious bacteria. The fastidious bacterial culture is maintained for a time period sufficient for the fastidious bacteria to multiply. The fastidious bacteria are then analyzed using PCR, DNA sequencing or microbiology characterization. The method is further described herein.

A variety of bacteria are challenged by the rigors of survival in the environment, especially fastidious bacteria such as one or more of the following, including, but not limited to: *Haemophilus influenza, Helicobacter pylori, Bordetella pertussis* and other *Bordetella* species, *B. fragilis, Mycobacterium tuberculosis, Legionella* species, *Spirochetes, Klebsiella* spp., *Brucella* species, *Francisella tularensis, Leptospira* species, *Borrelia burgdorferi, Bartonella* species, *Listeria* species, *Bordetella* species, *Eikenella corrodens, Pasteurella* species, *Haemophilus* species, *Chlamydia* species, *Camphylobacter* species, *Acinetobacter* species, *Mycoplasma* species, *Fusobacterium* species, *Corynebacteria* species, *Moraxella* species, *Pseudomonas* species, and *Neisseria* species, of which *F. tularensis* is used herein as exemplary. Fastidious bacteria are virtually impossible to culture using classical culturing approaches due to their nutritional and environmental requirements for robust growth of some bacterial pathogens.

*Francisella tularensis*, the causative agent of rabbit fever, is notoriously recalcitrant to culturing from environmental samples using traditional culturing approaches. *F. tularensis* has significant potential for use as a bioweapon. If *F. tularensis* were used as a bioweapon, it is imperative that this organism be successfully cultured from environmental, biocrime-relevant matrices. *F. tularensis* dispensed onto environmental matrices resulting from its deployment as a bioweapon has the potential to provide valuable evidence regarding attribution. Development of improved culturing approaches for culturing *F. tularensis* from environmental matrices enables the bioweapons to be amplified for downstream analyses, including PCR sequencing and microbiological characterization. Cultured bacterial bioweapons, recovered from biocrime scenes, can be analyzed to determine strain characteristics and, potentially, source attribution.

The method of the present invention can be used to culture pathogens, including gram-negative bacteria, and in particular, *F. tularensis*, by exploiting host cell-bacterial interactions that occur during the very early stages of bacterial pathogenesis. The method of the present invention can utilize factors secreted by immune cells. No eukaryotic cells are required in the presence of the bacteria being cultured. No engulfment (phagocytosis) of the bacteria by the eukaryotic cells is required. During performance of this immune cell-assisted bacterial culturing method, cytochalasin D, similar mycotoxin, or other chemical that inhibits engulfment of the bacteria by the macrophages, is added to the mixtures to prevent engulfment of the bacteria by the macrophages.

Provided in the examples herein below, are data showing successful culturing of one attenuated and one virulent strain of *F. tularensis* using the method of the present invention. *F. tularensis* extracted from sterile dust is also recoverable using the immune cell-assisted culturing approach. Preliminary Limits of Detection (LODs) are presented for these immune cell-assisted culturing procedures.

Methods and materials for use in the following examples for conducting experiments for *F. tularensis* are outlined in paragraphs [0022]-[0026].

Bacterial Strains.

*Francisella tularensis* LVS (Live Vaccine S train) was used from an in-house collection. Virulent *Francisella tularensis* WY96-3418 subspecies *tularensis* type A was obtained from American Type Culture Collection (ATCC; ATCC NR-644). Strains were stored at −80° C. in small volumes to prevent deleterious effects due to multiple freeze/thaw cycles.

Macrophages Cell Line.

RAW 264.7 mouse ascities macrophage cells were obtained from ATCC (ATCC TIB-71). The cell line was propagated and stored as recommended by the supplier.

Cell Culture.

The macrophages were continually passaged every 3 to 4 days in complete DMEM or complete EMEM media to maintain each cell line. One or two days prior to an experiment, the cells were split 1:3 or 1:5. On the day of the experiment, the cells were washed with incomplete DMEM or EMEM and then scraped into 2 ml of fresh incomplete DMEM or EMEM. The macrophages were then stained with trypan blue to obtain a viable cell count. The viable cell concentration was adjusted to about 2 e6 cells per ml and cytochalasin D was added to give the final concentration of 2 µg/mL 100 µl of cell suspension was then added to experimental wells and the plate is wrapped in parafilm and incubated at about 37° C. with 5% $CO_2$ for 2 hours prior to initiating the culturing procedure.

Culturing Procedure.

10 µl of cells were added to 100 µl of incomplete DMEM with cytochalasin D containing about 2 e5 macrophage cells in a 96 well tissue culture plate. Each sample was pipetted up and down ten times to mix at the time of the addition to the macrophages. The culture plate was covered and placed into a bag containing a damp laboratory pad, and then incubated at 37° C. with 5% $CO_2$. The tissue culture plate was incubated for 48 hours before dilution of the cells into 1×PBS (phosphate buffered saline)/0.1% BSA (bovine serum albumin) and plating onto Chocolate II agar (BD Biosciences). Larger volumes of cells and media can be used, as scaled-up methods, for these preparations. Chocolate II plates were incubated at 37° C. with 5% $CO_2$ until colonies were observed. Plates were checked for growth of 1-2 mm colonies and then all colonies were counted.

Extraction Procedure.

Samples of 100 mg of baked (sterile) Arizona Road Dust (ARD) were weighed out into 1.7 mL Eppendorf tubes or 2 mL Costar tubes. The ARD was baked at about 300° C. for about 30 minutes to achieve sterilization. 300 µl of extraction buffer (composed of PBS/0.1% BSA/0.05% Tween-20/0.167% Antifoam A) was added to each sample. 10 µl of diluted *F. tularensis* was added to samples and then rotated (approximately 30-60 rpm) for 20 minutes at room temperature. Alternatively, *F. tularensis* cells were added to the sterile ARD and allowed to dry; then 300 µL, of extraction buffer was added and the samples were rotated (approximately 30-60 rpm) for 20 minutes at room temperature. After rotation, each sample was allowed to gravity settle for 1 to 5 minutes, and then the extract was removed from the top or middle of the supernatant and diluted (if necessary) into 1× PBS/0.1% BSA for plating onto Chocolate II agar media (BD Biosciences) for analysis. This extraction procedure is adapted from a soil extraction procedure provided by Dr. Michael Cassler.

Example 1

Immune Cell-Assisted Culturing of *F. Tularensis* LVS

Initial studies were conducted using the vaccine strain *F. tularensis* LVS. The following media were tested for effectiveness for enhancing culturing of *F. tularensis* LVS in the presence of macrophages: Incomplete EMEM, Incomplete EMEM with cytochalasin D (cyto D), Incomplete DMEM, Incomplete DMEM with cyto D, Complete EMEM, Complete EMEM with cyto D, Complete DMEM and Complete DMEM with cyto D.

*F. tularensis* is usually engulfed by macrophages during early stages of pathogenesis [Anthony et al., (1991) *Infect Immun*, 59(9):3291-3296]; cytochalasin D (cyto D) paralyses actin polymerization functions [Casella et al., (1981) *Nature*, 293:302-395] and thereby prevents phagocytosis of the bacteria by the macrophages [Elliott and Winn, (1986), *Infect Immun*, 51(1):31-36]. Bacteria and macrophages were placed in the above cell culture media, incubated for about 48 hours and treated as described in the materials and methods hereinabove. The results from this study are presented in Table 1.

As shown in Panel A of Table 1 below, extended incubation of the bacteria with the macrophages (the incubation was extended from about 24 hours to about 48 hours; the data from the about 24 hour incubation study are not shown) prior to plating provides better immune cell-assisted bacterial culturing of *F. tularensis* LVS in incomplete DMEM with macrophages and in incomplete DMEM+cyto D with macrophages. The results of immune cell-assisted bacterial culturing for these two sample conditions are compelling. In both sample conditions, *F. tularensis* LVS exhibited too numerous to count (TNTC) colonies on some of the plates, and the samples had to be diluted (serially, 1:10, indicated as "Dil-2", "Dil-3" and so on in Table 10) to observe countable numbers of colonies. Bacterial growth appears excellent, although there is some scatter in the data for the plate counts.

TABLE 1

Panel A. Experimental Data

| | | VARIABLES | | | | | | | |
|---|---|---|---|---|---|---|---|---|---|
| | | COMPLETE | | | | INCOMPLETE | | | |
| | | Dil-2 | Dil-3 | Dil-4 | Dil-5 | Dil-2 | Dil-3 | Dil-4 | Dil-5 |
| DMEM | Media | 0x3 | 0x3 | 0x3 | 0x3 | 0x3 | 0x3 | 0x3 | 0x3 |
| | and Ba | 0x3 | 0x3 | 0x3 | 0x3 | 0x3 | 0x3 | 0x3 | 0x3 |
| | | 0x3 | 0x3 | 0x3 | 0x3 | 0x3 | 0x3 | 0x3 | 0x3 |
| | Media, | 1, 1, 0 | 0x3 | 0x3 | 0x3 | TNTC | TNTC | 198, 190, 230 | 59, 75, 58 |
| | Macroφ | 1, 0, 0 | 0x3 | 0x3 | 0x3 | TNTC | TNTC | 186, 260, 160 | 30, 32, 43 |

TABLE 1-continued

Panel A. Experimental Data

|  |  |  |  |  |  |  |  |  |  |
|---|---|---|---|---|---|---|---|---|---|
|  | and Ba | 0x3 | 0x3 | 0x3 | 0x3 | TNTC | 214, 182, 234 | 41, 50, 52 | 3, 6, 1 |
| EMEM | Media | 0x3 | 0x3 | 0x3 | 0x3 | 0x3 | 0x3 | 0x3 | 0x3 |
|  | and Ba | 0x3 | 0x3 | 0x3 | 0x3 | 0x3 | 0x3 | 0x3 | 0x3 |
|  |  | 0x3 | 0x3 | 0x3 | 0x3 | 0x3 | 0x3 | 0x3 | 0x3 |
|  | Media, | 0x3 | 0x3 | 0x3 | 0x3 | 0x3 | 0x3 | 0x3 | 0x3 |
|  | Macroφ | 0x3 | 0x3 | 0x3 | 0x3 | 0x3 | 0x3 | 0x3 | 0x3 |
|  | and Ba | 0x3 | 0x3 | 0x3 | 0x3 | 0x3 | 0x3 | 0x3 | 0x3 |

| | | | VARIABLES | | | | | | |
|---|---|---|---|---|---|---|---|---|---|
| | | | COMPLETE w/CYTO D | | | | INCOMPLETE w/CYTO D | | |
| | | | Dil -2 | Dil -3 | Dil -4 | Dil -5 | Dil -2 | Dil -3 | Dil -4 | Dil -5 |
| DMEM | Media | 0x3 | 0x3 | 0x3 | 0x3 | 0x3 | 0x3 | 0x3 | 0x3 |
| | and Ba | 0x3 | 0x3 | 0x3 | 0x3 | 0x3 | 0x3 | 0x3 | 0x3 |
| | | 0x3 | 0x3 | 0x3 | 0x3 | 0x3 | 0x3 | 0x3 | 0x3 |
| | Media, | 1, 0, 0 | 0x3 | 0x3 | 0x3 | TNTC | TNTC | 43, 48, 47 | 3, 4, 7 |
| | Macroφ | 0x3 | 0x3 | 0x3 | 0x3 | TNTC | 42, 49, 55 | 3, 9, 7 | 1, 0, 4 |
| | and Ba | 0x3 | 0x3 | 0x3 | 0x3 | 4, 4, 3 | 0x3 | 0, 1, 1 | 0x3 |
| EMEM | Media | 0x3 | 0x3 | 0x3 | 0x3 | 0x3 | 0x3 | 0x3 | 0x3 |
| | and Ba | 0x3 | 0x3 | 0x3 | 0x3 | 0x3 | 0x3 | 0x3 | 0x3 |
| | | 0x3 | 0x3 | 0x3 | 0x3 | 0x3 | 0x3 | 0x3 | 0x3 |
| | Media, | 0x3 | 0x3 | 0x3 | 0x3 | 0x3 | 0x3 | 0x3 | 0x3 |
| | Macroφ | 0x3 | 0x3 | 0x3 | 0x3 | 0x3 | 0x3 | 0x3 | 0x3 |
| | and Ba | 0x3 | 0x3 | 0x3 | 0x3 | 0x3 | 0x3 | 0x3 | 0x3 |

Immune cell-assisted culturing of *F. tularensis* LVS with about 48 hour incubation of bacteria with macrophages Analyses were performed in triplicate; colony counts on triplicate plates are separated by commas; if number of colonies are zero on all three plates it is indicated as "0×3"; "TNTC" indicates "too numerous to count" (i.e., there are greater than 300 bacterial colonies on the agar plate); "Dil-2" indicates 10 e-2 dilution of sample, "Dil-3" indicates 10 e-3 dilution of sample and so forth.

TABLE 1

Panel B.
Number of Ft Cells Added to Each Experimental Well - 48 hour experiments
VARIABLES

| | COMPLETE | INCOMPLETE | COMPLETE w/ CYTO D | INCOMPLETE w/ CYTO D |
|---|---|---|---|---|
| DMEM | 1, 0, 0 | 1, 1, 4 | 1, 0, 0 | 1, 1, 4 |
| EMEM | 5, 12, 1 | 4, 5, 1 | 5, 12, 1 | 4, 5, 1 |

Numbers of bacteria placed in the presence of macrophages

Three chocolate II agar plates (Plates 1, 2 and 3) were plated with 10 μL of *F. tularensis* LVS solution that was used in the evaluation of the samples shown in Panel A of Table 1.

Panel B of Table 1 shows data obtained from bacteria plated onto chocolate II agar plates ("untreated" bacteria) as both a positive control and an indication of the numbers of bacteria added to the samples. An estimated 50 cells were added in 10 μL; however, far fewer colonies were actually observed on the plates. Negative control samples ("100 μL media only", "100 μL media/10 μL PBS", "100 μL media with macrophages" and "100 μL media with macrophages/10 μL PBS") all behaved as expected (data not shown).

The evaluations of incomplete and complete DMEM media shown presented in Table 1 were repeated and this data obtained are presented in Table 2, below.

TABLE 2

Panel A. Experimental Data

| | | VARIABLES | | | | | | | |
|---|---|---|---|---|---|---|---|---|---|
| | | COMPLETE | | | | INCOMPLETE | | | |
| | | Dil -2 | Dil -3 | Dil -4 | Dil -5 | Dil -2 | Dil -3 | Dil -4 | Dil -5 |
| DMEM | Media | 0x3 | 0x3 | 0x3 | 0x3 | 0x3 | 0x3 | 0x3 | 0x3 |
| | and Ba | 1, 0, 0 | 0x3 | 0x3 | 0x3 | 0x3 | 0x3 | 0x3 | 0x3 |
| | | 0x3 | 0x3 | 0x3 | 0x3 | 0x3 | 0x3 | 0x3 | 0x3 |
| | Media, | 3, 4, 1 | 1, 2, 0 | 0x3 | 0x3 | TNTCx3 | TNTCx3 | 302, 200, 153 | 23, 31, 7 |
| | Macroϕ | 2, 1, 3 | 0, 1, 0 | 0x3 | 0x3 | TNTCx3 | TNTCx3 | TNTCx3 | 87, 57, 33 |
| | and Ba | 2, 6, 11 | 1, 2, 0 | 0x3 | 0x3 | TNTCx3 | TNTCx3 | 115, 56, 93 | 5, 15, 5 |

TABLE 2-continued

| | | Panel A. Experimental Data | | | | | | | |
|---|---|---|---|---|---|---|---|---|---|
| | | VARIABLES | | | | | | | |
| | | COMPLETE w/CYTO D | | | | INCOMPLETE w/CYTO D | | | |
| | | Dil -2 | Dil -3 | Dil -4 | Dil -5 | Dil -2 | Dil -3 | Dil -4 | Dil -5 |
| DMEM | Media and Ba | 0x3 | 0x3 | 0x3 | 0x3 | 0x3 | 0x3 | 0x3 | 0x3 |
| | | 0x3 | 0x3 | 0x3 | 0x3 | 0x3 | 0x3 | 0x3 | 0x3 |
| | | 0x3 | 0x3 | 0x3 | 0x3 | 0x3 | 0x3 | 0x3 | 0x3 |
| | Media, Macroϕ and Ba | 0x3 | 0x3 | 0x3 | 0x3 | TNTCx3 | TNTCx3 | TNTCx3 | 68, 164, 88 |
| | | 2, 0, 0 | 0x3 | 0x3 | 0x3 | TNTCx3 | TNTCx3 | 223, 132, 91 | 27, 2, 22 |
| | | 0x3 | 0x3 | 0x3 | 0x3 | TNTCx3 | TNTCx3 | 281, 217, 154 | 16, 7, 29 |

Immune cell-assisted culturing of *F. tularensis* LVS- about 48 hour incubation of bacteria with macrophages in DMEM Analyses were performed in triplicate; colony counts on triplicate plates are separated by commas; if the number of colonies were zero on all three plates it is indicated as "0×3"; "TNTC" indicates "too numerous to count" (i.e., there are greater than 300 bacterial colonies on the agar plate); "Dil-2" indicates 10 e-2 dilution of sample, "Dil-3" indicates 10 e-3 dilution of sample and so forth.

TABLE 2

| Panel B. Number of Ft Cells Added to Each Experimental Well - 48 hour repeat experiments | | | |
|---|---|---|---|
| VARIABLES | | | |
| COMPLETE | INCOMPLETE | COMPLETE w/ CYTO D | INCOMPLETE w/ CYTO D |
| DMEM 1, 0, 0 | 1, 1, 0 | 1, 0, 0 | 1, 1, 0 |

Numbers of bacteria placed in the presence of macrophages

Three chocolate II agar plates (Plates 1, 2 and 3) were plated with 10 μL of *F. tularensis* LVS solution that was used in the evaluation of the samples shown in Panel A of Table 2.

The data presented in Table 2, Panel A again show effective immune cell-assisted bacterial culturing of *F. tularensis* LVS occurs when the cells are placed in incomplete DMEM with macrophages. Enhanced bacterial growth appears both in the presence and absence of cytoD. Less data scatter is observed in the plate count data presented in Table 1.

Panel B of Table 2 shows data obtained from bacteria plated onto chocolate II agar plates ("untreated" bacteria) as both a positive control and an indication of the numbers of bacteria added to the samples. An estimated 50 cells were added in 10 μL; however, once again, far fewer colonies are observed on the plates. Negative control samples ("100 μL media only", "100 μL media/10 μL PBS", "100 μL, media with macrophages" and "100 μL media with macrophages/10 μL PBS") all behaved as expected (data not shown), as discussed above.

Example 2

Immune Cell-Assisted Culturing of Virulent *F. Tularensis*

Immune cell-assisted culturing was used to culture virulent *F. tularensis* (*F. tularensis* WY96-3418) with the same procedure used to successfully culture attenuated *F. tularensis* LVS, described above. *F. tularensis* WY96-3418 cells were co-cultured with macrophages in incomplete DMEM containing cytochalasin D at about 37° C. under 5% $CO_2$ for about 48 hours prior to plating onto chocolate II agar plates. Three samples containing bacteria and macrophages and three samples containing bacteria but lacking macrophages were evaluated. Additionally, one sample of *F. tularensis* LVS was evaluated in parallel as a control. Data from this experiment are presented in Table 3, below.

TABLE 3

| Panel A. Experimental Data | | | | | |
|---|---|---|---|---|---|
| Sample | Neat | −2 | −3 | −4 | −5 |
| 100 uL media only | N | | | | |
| 100 uL media/10 uL PBS | N | | | | |
| 100 uL media with macrophages | N | | | | |
| 100 uL media with macrophages/10 uL PBS | N | | | | |
| 100 uL media/10 uL (Ft LVS) | 0 | 0 | 0 | 0 | 0 |
| 100 ul media w/macrophages/10uL (Ft LVS) | TNTC | TNTCx3 | 34, 28, 37 | 2, 2, 5 | 0, 1, 0 |
| 100 uL media/10 uL (Ft WY96) | 0 | 0 | 0 | 0 | 0 |
| 100 uL media/10 uL (Ft WY96) | 0 | 0 | 0 | 0 | 0 |
| 100 uL media/10 uL (Ft WY96) | 0 | 0 | 0 | 0 | 0 |
| 100 uL media w/macrophages/10 uL (Ft WY96) | TNTC | TNTCx3 | 43, 44, 31 | 5, 5, 9 | 0, 0, 0 |
| 100 ul media w/macrophages/10 uL (Ft WY96) | TNTC | TNTCx3 | 245, 258, 193 | 26, 40, 25 | 4, 7, 5 |
| 100 ul media w/macrophages/10 uL (Ft WY96) | 179 | 98, 89, 79 | 6, 10, 6 | 1, 3, 3 | 0, 0, 0 |

Immune cell-assisted culturing of *F. tularensis* WY96-3418

Samples were evaluated in triplicate; colony counts on triplicate plates are separated by commas; "TNTC" indicates "too numerous to count" (i.e., there are greater than 300 bacterial colonies on the agar plate); "TNTCx3" indicates all three plates contained too many bacterial colonies to count. "−2" indicates 10 e-2 dilution of sample, "−3" indicates 10 e-3 dilution of sample and so forth. "Neat" indicates undiluted sample. "N" indicates no growth observed from the "Neat" sample. "Ft WY96"=*F. tularensis* WY96-3418.

TABLE 3

Panel B.

| Ft LVS dilution check ~100 colonies per 10 uL | | | Ft WY96 dilution check ~100 colonies per 10 uL | | |
|---|---|---|---|---|---|
| Plate 1 | 23 | PBS/0.1% | Plate 1 | 31 | PBS/0.1% |
| Plate 2 | 41 | BSA | Plate 2 | 4 | BSA |
| Plate 3 | 123 | | Plate 3 | 11 | |

Number of bacteria co-cultured with macrophages

Three plates (Plates 1, 2 and 3) were plated with 10 μL of *F. tularensis* LVS spiking solution (at left) or 10 μL of *F. tularensis* WY96-3418 spiking solution (at right) to indicate the number of bacteria added to the samples described in Panel A of Table 3. "Ft WY96"=*F. tularensis* WY96-3418.

As shown in Table 3, Panel A, culturing of *F. tularensis* WY96-3418 using incomplete DMEM+cyto D with macrophages (see reactions labeled "100 μL media w/macrophages/10 μL (Ft WY96)" in Panel A of Table 3) was successful. Parallel reactions lacking macrophages (see reactions labeled "100 μL media/10 μL (Ft WY96)") showed no growth. Parallel control samples ("100 μL media w/macrophages/10 μL (Ft LVS)" and "100 μL media/10 μL (Ft LVS)") behaved as expected, as discussed above. The plating data obtained using *F. tularensis* WY96-3418 show some scatter; nevertheless, it is evident that growth of this organism is stimulated by the presence of macrophages. Negative control samples ("100 μL media only", "100 μL media/10 μL PBS", "100 μL media with macrophages" and "100 μL media with macrophages/10 μL PBS") all behave as expected.

Panel B of Table 3 shows data obtained from bacteria plated onto chocolate II agar plates (i.e., "untreated" bacteria) as both a positive control and an indication of the numbers of bacteria added to the samples using the spiking samples. By bacterial titering, an estimated 100 cells were added in 10 μL; however, far fewer colonies are observed on these plates; this observation was also noted with *F. tularensis* LVS (as described above).

Example 3

Immune Cell Assisted Culturing of *F. Tularensis* WY96-3418 Extracted from Arizona Road Dust Several extraction solutions were evaluated for potential use to extract *F. tularensis* from dust samples (data not shown). These solutions included: 1.22 g/ml sucrose, 1.22 g/ml sucrose with 0.1% Triton X-100, 200 mM Trehalose/2 mM betaine, PBS/0.05% Tween 20/0.1% BSA with and without Antifoam A. The solution used for extraction of *F. tularensis* from dust must be compatible not only with the macrophages but also with the fragile, fastidious *F. tularensis* cells. Ultimately, a modified soil extraction protocol developed by Dr. Michael Cassler to extract *F. tularensis* from sterile Arizona Road Dust (ARD) for these studies was used. These studies were performed on *F. tularensis* WY96-3418.

In this study, 100 mg samples of baked Arizona Road Dust (ARD) were spiked with specified numbers of *F. tularensis* WY96-3418 cells. To each dust/bacteria sample, 300 mL of PBS/0.05% Tween 20/0.1% BSA containing Antifoam A was added. The samples were then placed at 30 rpm on a variable speed rotator at room temperature for 20 minutes. After allowing the dust to settle to the bottom of the tubes (approximately 1-5 minutes), a 10 μL aliquot of liquid was removed from each of the samples and co-cultured with macrophages for immune cell-assisted culturing using the conditions described above for virulent *F. tularensis*. Subsequent to co-culturing, material was plated onto chocolate II agar plates. The data obtained during this evaluation are presented in Table 4, below.

TABLE 4

Panel A. Experimental Data

| Sample | Neat | −2 | −3 | −4 | −5 |
|---|---|---|---|---|---|
| 100 uL media only | N | | | | |
| 100 uL media/10 uL PBS | N | | | | |
| 100 uL media with macrophages | N | | | | |
| 100 uL media with macrophages/10 uL PBS | N | | | | |
| 100 uL media/10 uL (sample 1) | 0 | 0 x 3 | 0 x 3 | 0 x 3 | 0 x 3 |
| 100 uL media/10 uL (sample 2) | 0 | 0 x 3 | 0 x 3 | 0 x 3 | 0 x 3 |
| 100 uL media/10 uL (sample 3) | 0 | 0 x 3 | 0 x 3 | 0 x 3 | 0 x 3 |
| 100 uL media/10 uL (sample 4) | 0 | 0 x 3 | 0 x 3 | 0 x 3 | 0 x 3 |
| 100 uL media/10 uL (sample 5) | 0 | 0 x 3 | 0 x 3 | 0 x 3 | 0 x 3 |
| 100 uL media w/macrophages/10 uL (sample 1) | TNTC | TNTC x 3 | TNTC x 3 | 291, 250, 296 | 34, 35, 31 |
| 100 uL media w/macrophages/10 uL (sample 2) | TNTC | TNTC x 3 | TNTC x 3 | TNTC x 3 | 170, 165, 144 |
| 100 uL media w/macrophages/10 uL (sample 3) | TNTC | TNTC x 3 | TNTC x 3 | TNTC x 3 | 77, 97, 78 |
| 100 uL media w/macrophages/10 uL (sample 4) | TNTC | TNTC x 3 | TNTC x 3 | 218, 226, 209 | 19, 18, 18 |
| 100 uL media w/macrophages/10 uL (sample 5) | TNTC | TNTC x 3 | TNTC x 3 | 56, 61, 68 | 13, 3, 5 |

Immune cell-assisted culturing of *F. tularensis* WY96-3418 extracted from dust

Samples were evaluated in triplicate; colony counts on triplicate plates are separated by commas; if the number of colonies are zero on all three plates it is indicated as "0x3"; "TNTC" indicates "too numerous to count" (i.e., there are greater than 300 bacterial colonies on the agar plate); "TNTCx3" indicates all three plates contained too many bacterial colonies to count. "−2" indicates 10 e-2 dilution of sample, "−3" indicates 10 e-3 dilution of sample and so forth. "Neat" indicates undiluted sample. "N" or "0" indicates no growth observed from the "Neat" sample; "Neat" samples were evaluated in singlet. "Ft WY96"=*F. tularensis* WY96-3418. Samples 1-5 are described in Panel C of Table 4.

TABLE 4

| Panel B. Check of bacterial spiking solutions | | |
|---|---|---|
| Ft Wy96 dilution check* ~1000 colonies per 10 uL | | |
| Plate 1 | 7 | PBS/0.1% |
| Plate 2 | 6 | BSA |
| Plate 3 | 9 | |
| Ft Wy96 dilution check* ~500 colonies per 10 uL | | |
| Plate 1 | 1 | PBS/0.1% |
| Plate 2 | 3 | BSA |
| Plate 3 | 4 | |

Spiking solutions were diluted 1/100 and plated to obtain about 10 colonies (for the about 1000 cells/10 μL spiking solution) and about 5 colonies (for the about 500 cells/10 μL spiking solution). Three plates (Plates 1, 2 and 3) were plated with 10 μL of *F. tularensis* WY96-3418 (Ft WY-96) spiking solution to check the number of bacteria added to the experimental samples described in Panel A.

TABLE 4

| Panel C. Summary of sample contents | |
|---|---|
| Sample # | Sample Description |
| 1 | 1000 Ft, 300 μl Buffer |
| 2 | 100 mg ARD, 1000 Ft, 300 μl Buffer |
| 3 | 100 mg ARD, 1000 Ft, 300 μl Buffer |
| 4 | 100 mg ARD, 500 Ft, 300 μl Buffer |
| 5 | 100 mg ARD, 500 Ft, 300 μl Buffer |

Summary of the constituents of Samples 1-5 used in this experiment.
ARD = Arizona Road Dust.

As shown in Table 4, Panel A, successful culturing of *F. tularensis* WY96-3418 bacteria extracted from ARD was observed using incomplete DMEM+cyto D with macrophages. Samples 1, 2 and 3 contain about 1000 *F. tularensis* cells and samples 4 and 5 contain about 500 cells (see Table 2, Panel C). In all cases, samples co-cultured with macrophages result in *F. tularensis* growth on chocolate II agar plates and reactions lacking macrophages result in no bacterial growth. Negative control samples ("100 μL media only", "100 μL media/10 μL PBS", "100 μL media with macrophages" and "100 μL media with macrophages/10 μL PBS") all behaved as expected, as discussed above.

Panel B of Table 4 shows data obtained from bacteria diluted and plated onto chocolate II agar plates as an indication of the numbers of bacteria added to the samples. Estimated bacterial titering that about 10 cells and 5 cells should appear on these plates; in this case, bacterial cell counts closely correspond to estimated numbers. Panel C of Table 4 presents a summary of the samples prepared for this study.

Example 4

Preliminary Determination of Limits of Detection for *F. Tularensis* LVS and *F. Tularensis* WY96-3418 Extracted from Dust and Cultured by Immune Cell-Assisted Culturing Studies were performed to determine preliminary Limits of Detection (LODs) for *F. tularensis* LVS and *F. tularensis* WY96-3418 extracted from baked ARD and cultured using immune cell-assisted culturing. The results from these experiments are presented in Tables 5 and 6, below.

TABLE 5

| Panel A. Experimental Data | | | | | | |
|---|---|---|---|---|---|---|
| Sample | Neat | -2 | -3 | -4 | -5 | Target Level |
| 100 uL media only | N | | | | | 0 |
| 100 uL media/10 uL buffer | N | | | | | 0 |
| 100 uL media with macrophages | N | | | | | 0 |
| 100 uL media with macrophages/10 uL buffer | N | | | | | 0 |
| 100 ul media w/macrophages/10 uL | TNTC | TNTC x 3 | TNTC x 3 | 179, 197, 184 | 26, 19, 28 | 500 |
| 100 ul media w/macrophages/10 uL | TNTC | TNTC x 3 | TNTC x 3 | 184, 187, 157 | 28, 0, 19 | 250 |
| 100 ul media w/macrophages/10 uL | TNTC | TNTC x 3 | TNTC x 3 | 220, 220, 249 | 28, 26, 14 | 250 |
| 100 ul media w/macrophages/10 uL | TNTC | TNTC x 3 | 36, 26, 35 | 6, 5, 3 | 0 x 3 | 100 |
| 100 ul media w/macrophages/10 uL | TNTC | TNTC x 3 | TNTC x 3 | 207, 186, 236 | 25, 29, 18 | 100 |
| 100 ul media w/macrophages/10 uL | 0 | 0 x 3 | 0 x 3 | 0 x 3 | 0 x 3 | 50 |
| 100 ul media w/macrophages/10 uL | 42 | 60, 85, 98 | 6, 8, 13 | 0, 2, 0 | 0 x 3 | 50 |
| 100 ul media w/macrophages/10 uL | 0 | 0 x 3 | 0 x 3 | 0 x 3 | 0 x 3 | 25 |
| 100 ul media w/macrophages/10 uL | 0 | 0 x 3 | 0 x 3 | 0 x 3 | 0 x 3 | 25 |
| 100 ul media w/macrophages/10 uL | 0 | 0 x 3 | 0 x 3 | 0 x 3 | 0 x 3 | 10 |
| 100 ul media w/macrophages/10 uL | 0 | 0 x 3 | 0 x 3 | 0 x 3 | 0 x 3 | 10 |

Preliminary determination of LOD for *F. tularensis* LVS extracted from dust and cultured using immune cell-assisted culturing Experimental samples were evaluated in triplicate; colony counts on triplicate plates are separated by commas; if number of colonies are zero on all three plates it is indicated as "0×3"; "TNTC" indicates "too numerous to count" (i.e., there are greater than 300 bacterial colonies on the agar plate); "TNTC×3" indicates all three plates contained too many bacterial colonies to count. "-2" indicates 10 e-2 dilution of sample, "-3" indicates 10 e-3 dilution of sample and so forth. "Neat" indicates undiluted sample. "N" indicates no growth observed from the "Neat" sample. Column labeled "Target Level" indicates number of bacteria introduced into co-culture with macrophages, based on bacterial titering.

TABLE 5

| Panel B. Check of bacterial spiking solutions | | | | | |
|---|---|---|---|---|---|
| Ft LVS dilution check ~500 colonies per 10 uL | | | Ft LVS dilution check ~50 colonies per 10 uL | | |
| Plate 1 | 93 | PBS/0.1% | Plate 1 | 8 | PBS/0.1% |
| Plate 2 | 73 | BSA | Plate 2 | 15 | BSA |
| Plate 3 | 76 | | Plate 3 | 12 | |

TABLE 5-continued

Panel B. Check of bacterial spiking solutions

| Ft LVS dilution check ~250 colonies per 10 uL | | | Ft LVS dilution check ~25 colonies per 10 uL | | |
|---|---|---|---|---|---|
| Plate 1 | 75 | PBS/0.1% | Plate 1 | 10 | PBS/0.1% |
| Plate 2 | 59 | BSA | Plate 2 | 9 | BSA |
| Plate 3 | 19 | | Plate 3 | 3 | |
| Ft LVS dilution check ~100 colonies per 10 uL | | | Ft LVS dilution check ~10 colonies per 10 uL | | |
| Plate 1 | 22 | PBS/0.1% | Plate 1 | 6 | PBS/0.1% |
| Plate 2 | 30 | BSA | Plate 2 | 2 | BSA |
| Plate 3 | 29 | | Plate 3 | 2 | |

Three plates (Plates 1, 2 and 3) were plated with 10 μL of each of the *F. tularensis* WY96-3418 (Ft WY-96) spiking solutions to check the number of bacteria added to the experimental samples described in Panel A. Spiking solutions were: about 500 cells/10 μL, about 250 cells/10 μL, about 100 cells/10 μL, about 50 cells/10 μL about 25 cells/10 μL and about 10 cells/10 μL.

Preliminary LODs for *F. tularensis* LVS and *F. tularensis* WY96-3418 extracted from dust were determined by spiking samples of baked ARD (100 mg) with the following numbers of *F. tularensis* cells: about 500, about 250, about 100, about 50, about 25 and about 10. Cells were extracted from the dust using the procedure previously described. Extracts were co-cultured with macrophages for immune cell-assisted cultur-

TABLE 6

Panel A. Experimental Data

| Sample | Neat | -2 | -3 | -4 | -5 | Target Level |
|---|---|---|---|---|---|---|
| 100 uL media only | N | | | | | 0 |
| 100 uL media/10 uL buffer | N | | | | | 0 |
| 100 uL media with macrophages | N | | | | | 0 |
| 100 uL media with macrophages/10 uL buffer | N | | | | | 0 |
| 100 ul media w/macrophages/10 uL | 0 | 0 x 3 | 0 x 3 | 0 x 3 | 0 x 3 | 500 |
| 100 ul media w/macrophages/10 uL | TNTC | 177, 246, 226 | 28, 32, 16 | 1, 2, 4 | 1, 1, 0 | 250 |
| 100 ul media w/macrophages/10 uL | TNTC | TNTC x 3 | TNTC x 3 | 86, 106, 108 | 12, 14, 7 | 250 |
| 100 ul media w/macrophages/10 uL | TNTC | TNTC x 3 | TNTC x 3 | TNTC x 3 | 50, 68, 49 | 100 |
| 100 ul media w/macrophages/10 uL | TNTC | TNTC x 3 | TNTC x 3 | TNTC x 3 | 53, 74, 75 | 100 |
| 100 ul media w/macrophages/10 uL | TNTC | TNTC x 3 | TNTC x 3 | TNTC x 3 | 73, 88, 94 | 50 |
| 100 ul media w/macrophages/10 uL | TNTC | TNTC x 3 | TNTC x 3 | 109, 72, 58 | 14, 15, 10 | 50 |
| 100 ul media w/macrophages/10 uL | 0 | 0 x 3 | 0 x 3 | 0 x 3 | 0 x 3 | 25 |
| 100 ul media w/macrophages/10 uL | TNTC | TNTC x 3 | TNTC x 3 | TNTC x 3 | 21, 30, 23 | 25 |
| 100 ul media w/macrophages/10 uL | 0 | 0 x 3 | 0 x 3 | 0 x 3 | 0 x 3 | 10 |
| 100 ul media w/macrophages/10 uL | 0 | 0 x 3 | 0 x 3 | 0 x 3 | 0 x 3 | 10 |

Preliminary determination of LOD for *F. tularensis* WY96-3418 extracted from dust and cultured using immune cell-assisted culturing Samples were evaluated in triplicate; colony counts on triplicate plates are separated by commas; if number of colonies are zero on all three plates it is indicated as "0×3"; "TNTC" indicates "too numerous to count" (i.e., there are greater than 300 bacterial colonies on the agar plate); "TNTC×3" indicates all three plates contained too many bacterial colonies to count. "−2" indicates 10 e-2 dilution of sample, "−3" indicates 10 e-3 dilution of sample and so forth. "Neat" indicates undiluted sample. "N" indicates no growth observed from the "Neat" sample. Column labeled "Target Level" indicates number of bacteria introduced into co-culture with macrophages, based on bacterial titering.

TABLE 6

Panel B. Check of bacterial spiking solutions

| Ft Wy96 dilution check ~500 colonies per 10 uL | | | Ft Wy96 dilution check ~50 colonies per 10 uL | | |
|---|---|---|---|---|---|
| Plate 1 | 137 | PBS/0.1% | Plate 1 | 12 | PBS/0.1% |
| Plate 2 | 169 | BSA | Plate 2 | 6 | BSA |
| Plate 3 | 218 | | Plate 3 | 9 | |
| Ft Wy96 dilution check ~250 colonies per 10 uL | | | Ft Wy96 dilution check ~25 colonies per 10 uL | | |
| Plate 1 | 82 | PBS/0.1% | Plate 1 | 3 | PBS/0.1% |
| Plate 2 | 59 | BSA | Plate 2 | 4 | BSA |
| Plate 3 | 23 | | Plate 3 | 7 | |
| Ft Wy96 dilution check ~100 colonies per 10 uL | | | Ft Wy96 dilution check ~10 colonies per 10 uL | | |
| Plate 1 | 27 | PBS/0.1% | Plate 1 | 4 | PBS/0.1% |
| Plate 2 | 4 | BSA | Plate 2 | 1 | BSA |
| Plate 3 | 20 | | Plate 3 | 2 | | ing using the conditions described above and then plated onto chocolate II agar plates.

The data indicating the preliminary LOD for *F. tularensis* LVS extracted from ARD are presented in Table 5.

As shown in Table 5, Panel A, a preliminary LOD for *F. tularensis* LVS was measured and extracted from dust as about 100 organisms. Again, the plating data obtained using *F. tularensis* LVS show some scatter. Negative control samples ("100 μL media only", "100 mL media/10 μL PBS", "100 μL media with macrophages" and "100 μL media with macrophages/10 μL PBS") all behaved as expected.

Panel B of Table 5 shows data obtained from bacteria diluted and plated onto chocolate II agar plates as an indication of the numbers of bacteria added to the samples. All spiking solutions (about 500 cells/10 μL, about 250 cells/10 μL, about 100 cells/10 μL, about 50 cells/10 μL, about 25 cells/10 μL and about 10 cells/10 μL) were checked. As observed previously, plate counts for *F. tularensis* do not always come out as expected given previous titering results.

The data indicating the preliminary LOD for *F. tularensis* WY96-3418 extracted from ARD are presented in Table 6.

Table 6, Panel A, presents data obtained from this evaluation. Plating data from samples containing about 500 cells and about 250 cells are surprising; significantly greater bacterial growth is expected on these plates. Nevertheless, these data were used to determine a preliminary LOD for *F. tularensis* WY96-3418 (Ft WY-96) extracted from dust as about 50 organisms. Again, the plating data obtained using *F. tularensis* WY96-3418 show some scatter. Negative control samples ("100 μL media only", "100 mL media/10 μL PBS", "100 μL media with macrophages" and "100 μL media with macrophages/10 μL PBS") all behaved as expected, as discussed above.

Panel B of Table 6 shows data obtained from bacteria diluted and plated onto chocolate II agar plates as an indication of the numbers of bacteria added to the samples. All spiking solutions (about 500 cells/10 μL, about 250 cells/10 μL, about 100 cells/10 μL, about 50 cells/10 μL, about 25 cells/10 μL and about 10 cells/10 μL) were checked. As observed previously, plate counts for *F. tularensis* do not always come out as expected given previous results.

Example 5

Pre-Validation of Combined Procedures: Immune Cell-Assisted Culturing of *F. Tularensis* Extracted from Baked ARD The performance of the dust extraction procedure was evaluated in combination with immune cell-assisted bacterial culturing to determine the reliability of these two methods. An evaluation was performed during which two technicians performed an independent analysis to determine a preliminary, but reliable limit of detection for these combined procedures. Baked ARD samples were spiked with known numbers of *F. tularensis* cells; these samples were then extracted and 10 μL samples of the extract were added to 100 μL of macrophages in incomplete DMEM with cytochalasin D and treated as previously described.

TABLE 7

Results of combined immune cell-assisted culturing pre-validation of *F. tularensis* WY96-3418
Ft Wy96-3418 Summary Results

| Number of Spiked Cells | Positive | Total |
|---|---|---|
| 500 | 4 (100%) | 4 |
| 100 | 11 (92%) | 12 |
| 50 | 1 (25%) | 4 |
| 0 | 0 | 12 |

TABLE 8

Ft LVS Summary Results

| Number of Spiked Cells | Positive | Total |
|---|---|---|
| 500 | 6 (100%) | 6 |
| 100 | 13 (72%) | 18 |
| 50 | 4 (66%) | 6 |
| 0 | 0 | 18 |

Four studies were performed in the pre-validation using Ft WY96-3418 to ensure that the virulent *F. tularensis* strain performed similar to *F. tularensis* LVS. At the highest level (500 Ft cells) the Ft WY96-3418 and Ft LVS were both detected 100%. At the LOD level of 100 Ft cells, Ft WY96-3418 is positive in 92% of samples tested, a better result than *F. tularensis* LVS which was positive in 72% of samples. Below the LOD at 50 Ft cells both strains perform poorly at 25% (Ft WY96-3418) and 66% (Ft LVS) positive. In addition to spiked samples, thirty blanks (100 mg ARD and extraction buffer) were tested to determine the false positive and cross-contamination rate. All blank samples produced the expected negative results.

Results ten positive at LOD 10 out of eleven tested samples. Over the course of three studies, eleven total samples were tested at a limit of detection (LOD) of 10 Ft WY96 in 100 mg of sterile Arizona Road Dust (ARD). Each sample was extracted per the extraction SOP and then in a deviation to the culturing SOP the entire extract was added in 10 μl increments to thirty wells containing macrophage cells. For field sample extracts, the most important aspect is finding the target organism and not a comparable count so an alternative protocol was added to address this issue.

Example 6

Identification of Factors for Enhanced Culturing of Bacteria

Identification of the factors elaborated by macrophages is an important first step in developing the use of such factors for culturing fastidious pathogenic bacteria from diagnostic samples and samples from biocrime scenes. Cytokines are proteins secreted by immune cells, including macrophages, which aid in the immune response. Several cytokines, such as IL-1β, IL-6 and TNF-α, are well-characterized pro-inflammatory molecules that are known to increase the proliferation of immune cells both in vitro and in vivo. The effect of cytokines on bacterial proliferation has not been well studied; however IL-1β has been shown to increase the growth of *Staphylococcus aureus* and *Acinetobacter* spp. in vitro, while IL-6 has been shown to increase the growth of *Pseudonomas aeruginosa*. [Meduri, G U, S Kanangat, J Stefan, E Tolley, D Schaberg. Cytokines IL-6 and TNF-α enhance in vitro growth of bacteria. Am. J. Respir. Crit. Care Med. 1999; 160: 961-967].

Cytokine secretion by macrophages were the factors responsible for the observed increase in *F. tularensis* growth. Macrophage-only conditioned media, macrophage plus FT-LVS (vaccine strain) conditioned media, and media only (negative control) were analyzed against a panel of 10 cytokines and chemokines known to be secreted by macrophages using a Luminex MAGPIX instrument. The 10-plex panel included IFN-γ, IL-10, IL-12p40, IL-12p70, IL-1α, IL-1β, IL-6, MCP-1, MIP and TNF-α. Five cytokines were found to be present in both the macrophage-only and macrophage plus FT-LVS media: MCP-1, MIP-1α and TNF-α were secreted at high levels (above 10,000 pg/ml) in both media types, while IL-6 and IL-1β were secreted at a low level (between 16-80 pg/ml). None of the cytokines tested were present in the media-only sample. Presence of a cytokine was in the macrophage-conditioned media and in the FT-LVS plus macrophage-conditioned media, but was absent in the negative control media. Therefore, cytokine can be involved in *F. tularensis* proliferation and in the proliferation of other fastidious bacteria. Each fastidious bacterium has a set of factors that promote growth for that bacterium. Some cytokines are secreted into all media types that have been found to increase *F. tularensis* proliferation.

As it applies to the present invention, a variety of eukaryotic cell types are available for culturing for the development of IC-ABC procedures. These eukaryotic cells to help culture low numbers of *B. anthracia* spores isolated by laser capture microdissection.

The following cell lines also showed stimulation for bacterial growth:
(1) RAW 264.7 (murine macrophage). These cells are easy to culture, easy to passage by scraping. Able to attain 2 e6 cells/ml for several samples with 1 or 2 flasks. This line was used by far most frequently during the IC-ABC experiments.

(2) mSXL 5 (B cell hybridoma). These cells are easy to culture. Cells are centrifuged to wash in experiments. Used RPMI1640 for experiments. Easy to attain desired concentration for many samples.

(3) HeLa S3 (human cervix adenocarcinoma). This cell line spreads out when it's attached to growth surface of flask. Cells can be scraped or trypsinized. Cell count is on the lower side, must use several flasks for a few samples to get 2 e6 cells/mL.

(4) A549 (human lung carcinoma). This cell line spreads out when it's attached to growth surface of flask. Cells should be trypsinized. Cell count is low, must use several flasks for a few samples to get 2 e6 cells/mL.

(5) Fcwf-4 (feline fetus macrophage). This cell line is not ideal. It is slow to grow, spreads out when it's attached to growth surface of flask. Cells should be trypsinized. Cell count is low, must use several flasks for a few samples to get 2 e6 cells/mL.

In addition to the media that is disclosed herein, serum free media can be used in the method of the present invention.

Each of the patents, patent applications and articles cited herein is incorporated by reference. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Because many possible embodiments may be made of the invention without departing from the scope thereof, it is to be understood that all matter herein set forth or shown in the accompanying drawings is to be interpreted as illustrative, and not in a limiting sense.

What is claimed is:

1. A method of culturing fastidious bacteria comprising the steps of:
    a) providing a conditioned cell culture medium in which mammalian macrophages have been cultured that is substantially free of said cultured macrophages wherein a mycotoxin is added to said medium to prevent engulfment of said fastidious bacteria by said culture macrophages;
    b) culturing fastidious bacteria in said medium; and
    c) maintaining said fastidious bacterial culture for a time period sufficient for said fastidious bacteria to multiply.

2. The method of claim 1, wherein said fastidious bacteria is selected from the group consisting of one or more of *Haemophilus influenza*, *Helicobacter pylori*, *B. fragilis*, *Mycobacterium tuberculosis*, *Legionella* species, *Spirochetes*, *Klebsiella* spp., *Brucella* species, *Francisella tularensis*, *Leptospira* species, *Borrelia burgdorferi*, *Bartonella* species, *Listeria* species, *Bordetella* species, *Eikenella corrodens*, *Pasteurella* species, *Haemophilius* species, *Chlamydia* species, *Camphylobacter* species, *Acinetobacter* species, *Mycoplasma* species, *Fusobacterium* species, *Corynebacteria* species, *Moraxella* species, *Pseudomonas* species, and *Neisseria* species.

3. The method of claim 1, wherein said fastidious bacteria is a pathogen.

4. The method of claim 3, wherein said pathogen is *Francisella tularensis*.

5. The method of claim 1, wherein said fastidious bacteria is gram-negative.

6. The method of claim 1, further comprising the step of:
    analyzing said bacteria using PCR, DNA sequencing or microbiology characterization.

7. The method of claim 1, wherein said mycotoxin is cytochalasin D.

8. The method of claim 1, wherein said conditioned cell culture medium contains at least one secreted factor from said macrophage wherein said at least one factor promotes the growth of said fastidious bacteria.

9. The method of claim 8, wherein said at least one factor is a cytokine.

10. The method of claim 8, wherein said at least one secreted factor is selected from the group consisting of one or more of MCP-1, MIP-1α, TNF-α, IL-6, and IL-1β.

11. An immune cell-assisted bacterial culturing method comprising the steps of:
    a) obtaining macrophage cells;
    b) propagating said macrophage cells in a medium;
    c) filtering said macrophage cells to remove said macrophage cells from said medium creating a filtered, condition medium containing at least one factor secreted from said macrophage cells and substantially no cells;
    d) introducing said *Francisella tularensis* to said filtered, conditioned medium;
    e) maintaining said *Francisella tularensis* in said filtered, condition medium under time, temperature, and atmospheric conditions suitable for culturing said *Francisella tularensis*; and
    f) assaying said *Francisella tularensis* for analysis.

12. The method of claim 11, further comprising the step of:
    analyzing said *Francisella tularensis* using PCR, DNA sequencing or microbiology characterization.

13. The method of claim 11, wherein said *Francisella tularensis* is not engulfed by said cells.

14. The method of claim 11, further comprising the step of:
    adding a mycotoxin to said filtered, conditioned medium to prevent engulfment of said *Francisella tularensis* by said cells.

15. The method of claim 14, wherein said mycotoxin is cytochalasin D.

16. The method of claim 11, wherein said at least one factor promotes the growth of said *Francisella tularensis*.

17. The method of claim 11 wherein said at least one factor is selected from the group consisting of one or more of MCP-1, MIP-1α, TNF-α, IL-6, and IL-1β.

18. A method of culturing fastidious bacteria comprising the steps of:

a) providing a conditioned cell culture medium in which eukaryotic cells have been cultured that is substantially free of said cultured cells and contains at least one factor secreted from said cells;
b) culturing fastidious bacteria in said medium, wherein the fastidious bacteria are gram negative; and
c) maintaining said fastidious bacterial culture under time, temperature, and atmospheric conditions suitable for culturing said fastidious bacteria, wherein said at least one factor promotes the growth of said fastidious bacteria; and
d) assaying said fastidious bacteria for analysis.

\* \* \* \* \*

UNITED STATES PATENT AND TRADEMARK OFFICE
CERTIFICATE OF CORRECTION

| | | |
|---|---|---|
| PATENT NO. | : 9,051,558 B2 | Page 1 of 1 |
| APPLICATION NO. | : 13/972888 | |
| DATED | : June 9, 2015 | |
| INVENTOR(S) | : Kelly Brown et al. | |

It is certified that error appears in the above-identified patent and that said Letters Patent is hereby corrected as shown below:

Title page, item [73], delete "MI", and replace with -- MO --

Signed and Sealed this
Twentieth Day of October, 2015

Michelle K. Lee
*Director of the United States Patent and Trademark Office*